United States Patent
Thiel et al.

(10) Patent No.: US 10,254,111 B2
(45) Date of Patent: Apr. 9, 2019

(54) DEVICE FOR OPTICAL 3D MEASURING OF AN OBJECT

(71) Applicant: DENTSPLY SIRONA inc., York, PA (US)

(72) Inventors: Frank Thiel, OberRamstadt (DE); Gerrit Kocherscheidt, Walldorf (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/575,834

(22) PCT Filed: May 23, 2016

(86) PCT No.: PCT/EP2016/061533
§ 371 (c)(1),
(2) Date: Nov. 21, 2017

(87) PCT Pub. No.: WO2016/188939
PCT Pub. Date: Dec. 1, 2016

(65) Prior Publication Data
US 2018/0299262 A1     Oct. 18, 2018

(30) Foreign Application Priority Data
May 22, 2015   (DE) .................. 10 2015 209 402

(51) Int. Cl.
*G01B 11/25*     (2006.01)
*A61B 1/24*     (2006.01)
(Continued)

(52) U.S. Cl.
CPC ...... *G01B 11/2513* (2013.01); *A61B 1/00009* (2013.01); *A61B 1/00193* (2013.01);
(Continued)

(58) Field of Classification Search
CPC . A61B 1/00172; A61B 1/00188; A61B 1/247; A61C 9/006; A61C 9/0066; G01B 11/2527; G01B 11/2513
See application file for complete search history.

(56) References Cited

U.S. PATENT DOCUMENTS 6,229,913 B1 * 5/2001 Nayar ................ G02B 27/2278
                                                       382/154
7,852,492 B2 * 12/2010 Berner ............... G01B 11/2513
                                                       356/605
(Continued)

FOREIGN PATENT DOCUMENTS

WO   WO-2008125605 A2 * 10/2008   ........ G01B 11/2504
WO   WO-2010145669 A1 * 12/2010   ........... A61B 5/0068

*Primary Examiner* — Sang H Nguyen
(74) *Attorney, Agent, or Firm* — DENTSPLY SIRONA Inc.

(57) ABSTRACT

The invention relates to a device for optical 3D measurement of an object using an optical depth-scanning measurement method, comprising at least two light sources, at least two optical means for producing textured patterns and at least one recording means. A first pattern is produced with the aid of a first optical means and projected onto the object to be recorded as a first projection beam. A second pattern is produced with the aid of a second optical means and projected onto the object to be recorded as a second projection beam. The imaging optics is controlled and adjusted in such a way that a sharp focal plane is incrementally varied along an optical axis of the device.

10 Claims, 3 Drawing Sheets

(51) Int. Cl.
   *A61B 1/00*   (2006.01)
   *A61B 1/06*   (2006.01)
(52) U.S. Cl.
   CPC .............. *A61B 1/0646* (2013.01); *A61B 1/24* (2013.01); *G01B 11/25* (2013.01)

(56) References Cited

U.S. PATENT DOCUMENTS

| | | | | |
|---|---|---|---|---|
| 8,577,212 | B2* | 11/2013 | Thiel | A61B 5/0068 348/46 |
| 8,878,905 | B2* | 11/2014 | Fisker | A61B 5/0068 348/46 |
| 2010/0079581 | A1* | 4/2010 | Russell | H04N 13/254 348/46 |
| 2010/0189341 | A1* | 7/2010 | Oota | A61B 1/0019 382/154 |
| 2015/0029309 | A1* | 1/2015 | Michaeli | G02B 21/0028 348/46 |
| 2015/0347833 | A1* | 12/2015 | Robinson | G01B 11/25 348/77 |
| 2016/0003613 | A1* | 1/2016 | Atiya | G01B 11/25 356/612 |
| 2016/0015489 | A1* | 1/2016 | Atiya | A61C 9/0053 433/29 |
| 2016/0231551 | A1* | 8/2016 | Berner | A61C 9/006 |
| 2018/0125338 | A1* | 5/2018 | Pfeiffer | A61C 9/0066 |

\* cited by examiner

DEVICE FOR OPTICAL 3D MEASURING OF AN OBJECT

TECHNICAL FIELD

The invention relates to a device for optical 3D measurement of an object using an optical depth-scanning measurement method, comprising at least two light sources, at least two optical means for producing textured patterns and at least one recording means, wherein a first pattern is produced with the aid of a first optical means and projected onto the object to be recorded as a first projection beam, wherein a second pattern is produced with the aid of a second optical means and projected onto the object to be recorded as a second projection beam, wherein the first pattern and the second pattern are reflected back from the object as observation beams and recorded by the recording means in order to create a 3D data set of the object.

BACKGROUND OF THE INVENTION

A number of devices for optical 3D measurement are known from the state of the art.

WO 2008/125605 A2 discloses a method and an arrangement for the optical imaging of objects, in particular in the field of microscopy, wherein a first illumination distribution and a second illumination distribution are projected onto the object. The two projected illumination distributions can differ by 180° with respect to their phase. The illumination structures are simultaneously projected onto the object and are characterized by polarization or by spectral characteristics.

EP 2 051 042 B1 discloses an optical coherence method, in which at least two patterns of parallel stripes are superimposed, thereby creating a moiré pattern that is projected onto the surface of the object. The three-dimensional shape of the object is determined on the basis of the scan positioning of the moiré lines.

WO 2010/145669 A1 discloses a confocal surveying method, in which a checkerboard-like projection pattern is projected onto the object. The temporal progression of the contrast is determined as well, to obtain depth information for the object. The temporally varied pattern is generated by using mechanically driven screening means, such as an aperture wheel.

One disadvantage of this method is that the temporally varied pattern is produced by using the mechanically driven screening means, as a result of which measuring errors can occur.

The task of the present invention, therefore, is to provide a device that enables reliable and accurate measurement of the object.

SUMMARY OF THE INVENTION

The invention relates to a device for optical 3D measurement of an object using an optical depth-scanning measurement method, comprising at least two light sources, at least two optical means for producing textured patterns and at least one recording means, wherein a first pattern is produced with the aid of a first optical means and projected onto the object to be recorded as a first projection beam, wherein a second pattern is produced with the aid of a second optical means and projected onto the object to be recorded as a second projection beam. In doing so, the first pattern and the second pattern are reflected back from the object as observation beams and recorded by the recording means in order to create a 3D data set of the object, wherein the device comprises imaging optics for the projection of the patterns onto the object, wherein the imaging optics is controlled and adjusted in such a way that a sharp focal plane is incrementally varied along an optical axis of the device, wherein, at each scan position of the sharp focal plane, the first pattern is projected to produce a first optical image and then at least the second pattern is projected onto the object to produce a second optical image. The device is configured in such a way that the first light source and the second light source are activated in an alternating manner by means of a control, wherein the first pattern and the second pattern are projected onto the object in an alternating manner, wherein the first projection beam of the first pattern and the second projection beam of the second pattern are deflected into one common illumination direction toward the object with the aid of a first beam splitter.

The device for optical 3D measurement can be a camera that is integrated in a conventional housing in the form of a handpiece. The optical depth-scanning measurement method may be a confocal measurement method with the depth-from-defocus approach. For this purpose, checkerboard-like projection patterns are projected onto the object in an alternating manner. The depth information of the measuring points on the object is subsequently deter-mined by determining a value for the focus, i.e. the sharpness, of the projected checkerboard pattern. On the basis of this value, the distance of a sharp focal plane relative to the surface of the object may be determined.

The light sources can, for example, be color LEDs, white LEDs or laser LEDs. The optical means can be a projection grating or a projection mask that produces the projection pattern. The optical means can also be a digital light projector made of liquid elements (LCD), which is controlled as appropriate and produces the projection pattern. The recording means can be a conventional optical sensor, such as a CCD sensor. The first pattern and the second pattern are thus projected onto the object in an alternating manner. The focusing optics are adjustable and focus the projected patterns onto the established sharp focal plane, which is incrementally varied along the optical axis so that the entire object can be scanned. The scan positions can have a distance of 0.1 mm from one another, for example, so that a depth-scanning of an object in the height of 10 mm can be performed with 100 scan positions. The resolution along the optical axis is therefore defined by this distance. The adjustment of the focusing optics can be carried out continuously, whereby only the image data of the images are read discretely from the defined scan positions.

For every scan position, therefore, the first image with the first projected pattern and at least one second image with the second projected pattern are produced. As a result, according to this method, the intensity and the intensity variation can be recorded for every change of the sensor. In this way, the difference between the intensity values in the first image and the second image can be determined and, from that, the contrast or the sharpness of the two images can be determined. On the basis of a contrast value or a sharpness, a focal distance of a surface of the object to be measured relative to the plane of sharp focus can then be determined. If the object surface to be measured deviates from the plane of sharp focus, the object appears blurred in the image. If the focal distance of the plane of sharp focus, i.e. the focal length of the focusing optics, is known, then the distance of the object surface relative to the camera can be calculated. In order to determine the three-dimensional image data of the object according to the depth-from-defocus measurement method (DFD), the images recorded in the different scan positions are merged with one another to determine the three-dimensional image data of the object. For each pixel, for example, the intensity value is plotted as a function of a frame number and thus as a function of the time and the focal position. If the object is not in the focal position, the contrast deteriorates. If the object is in the focal position, the contrast is at its maximum. The image with the maximum contrast is thus recorded in the focal position of the camera. In this way, the distance of the object relative to the camera is determined.

The control of the device is configured to activate the two light sources in an alternating manner at a high frequency, so that the two patterns are projected onto the object in an alternating manner. The beam splitter can be a conventional prism that deflects the first projection beam of the first pattern and the second projection beam of the second pattern, which come from different directions, into one common illumination direction.

One advantage of this device is that the pattern is changed without the use of mechanical means. Measuring errors, which may be caused by such mechanical means, can thus be prevented.

A further advantage of this device is that, as a result of the electronic switching between the two light sources, a much higher frequency of the changing pattern can be produced than when mechanical means are used. This allows the time required for the measurement or the number of scan positions to be reduced, thus improving the resolution of the 3D data set generated for the object.

The device can advantageously comprise a third light source in addition to the second light source, a third optical means and a second beam splitter, wherein a third pattern is produced with the aid of the third optical means and a third projection beam is deflected into the common illumination direction with the aid of the second beam splitter.

The first pattern, the second pattern and the third pattern are thus consecutively projected onto the object in an alternating manner. By using a plurality of patterns, the resolution in lateral direction can be improved.

The first beam splitter and the second beam splitter can advantageously be combined into a dichroic prism, wherein the first, second and third projection beam are deflected into the common illumination direction by means of this dichroic prism.

The dichroic prism is an optical prism that splits a light beam into two beams of different spectra or colors. It is usually made of glass, wherein certain surfaces are provided with dichroic mirrors, which reflect or allow the transmission of light depending on the wavelength of said light. The use of such a dichroic prism thus allows three projection beams coming from different directions to be deflected into one common illumination direction. The first projection beam can have a red component, the second projection beam can have a green component and the third projection beam can have a blue component. The colored projection beams can be produced, for example, by using colored LEDs or by using color filters, which are disposed downstream of a light source.

The optical means for producing the patterns can advantageously be optical gratings or liquid-crystal elements (LCD).

The optical grating or the LCD thus produce the projected pattern. The LCD is controlled accordingly.

The projected patterns can advantageously be in the form of parallel stripes.

In accordance with the depth-scanning methods used, therefore, the contrast and with it the depth information is determined in the transition area between the dark and light parallel stripes.

When there are only two light sources, the width of the parallel stripes can advantageously correspond to the distance between the parallel stripes.

The first pattern and the second pattern are thus supplemented with the parallel stripes, so that a dark stripe of the second pattern is disposed at the scan position of a light stripe of the first pattern and vice versa. As a result, therefore, the contrast and the depth information are determined for the same measuring points of the object, which allows the measurement accuracy to be improved.

The projected patterns can advantageously have the form of a checkerboard with square pattern elements.

Contrast values and with them depth information are thus determined in the transition areas between the light pattern elements and the dark pattern elements by means of the checkerboard form of the projected patterns, which allows the resolution of the 3D data set of the object to be improved.

Advantageously, the first pattern can be a first checkerboard-like pattern and the second pattern can be a second checkerboard-like pattern, wherein a dark square pattern element of the second checkerboard-like pattern is disposed at the scan position of a light square pattern element of the first checkerboard-like pattern and vice versa, so that the light pattern elements and the dark pattern elements of the two checkerboard-like patterns are respectively projected onto the object in an alternating manner.

The two checkerboard-like patterns thus complement each other, so that the contrast values and with them the depth information for the same measuring points on the object surface are determined; this allows potential measuring errors to be reduced.

The device can advantageously comprise a control, which switches the light sources on and off in an alternating manner at a frequency of at least 3000 Hz.

With the relatively high frequency of the changing patterns, the object can be measured with the depth-scanning method in a short amount of measuring time.

The frequency can advantageously be between 5000 Hertz and 10000 Hertz.

In one example of the device, the frequency is 8000 Hertz. In this case, the entire depth scan of the whole object is carried out at 20 Hertz, wherein both patterns are respectively projected for each of the 200 depth positions and both images are recorded. With such a fast measurement, the device in the form of a hand-held camera can be held freely, because, for a complete measurement at 20 Hertz, the movements of a hand-held camera relative to the objects, such as the teeth of a patient or a tooth model, are negligible.

To produce the optical image or scan, at least 100 scan positions of the sharp focal plane can advantageously be set and measured incrementally.

If there are 100 scan positions, the distance between the scan positions can be 0.2 mm, for example, because the typical depth-scanning range for measuring teeth is 20 mm.

At least 200 scan positions of the sharp focal plane can advantageously be set per image.

The resolution along the optical axis is improved by the greater number of scan positions. The distance between the scan positions can be 0.1 mm, for example.

Contrast values between the light and the dark elements of the patterns can advantageously be determined for each optical image, whereby 3D depth information for the object is determined on the basis of the contrast values.

In accordance with the depth scanning methods used, contrast values are determined in the transition areas between the light and the dark elements of the patterns, and from them then the depth information.

A profile of the contrast values for all set scan positions of the plane of sharp focus can advantageously be determined for every measuring point of the object, whereby a maximum value of this profile, which represents the depth information of the object surface for this measuring point of the object, is subsequently determined.

In this way, therefore, the depth information for the measuring points of the object surface in the boundary area between the dark and the light elements is determined. The evaluation of the 3D data set for the object from the individual optical images of the changed patterns can be performed with the aid of a computer.

BRIEF DESCRIPTION OF THE DRAWINGS

The invention is explained with reference to the drawings. The drawings show.

DETAILED DESCRIPTION OF THE INVENTION

Figure 1:
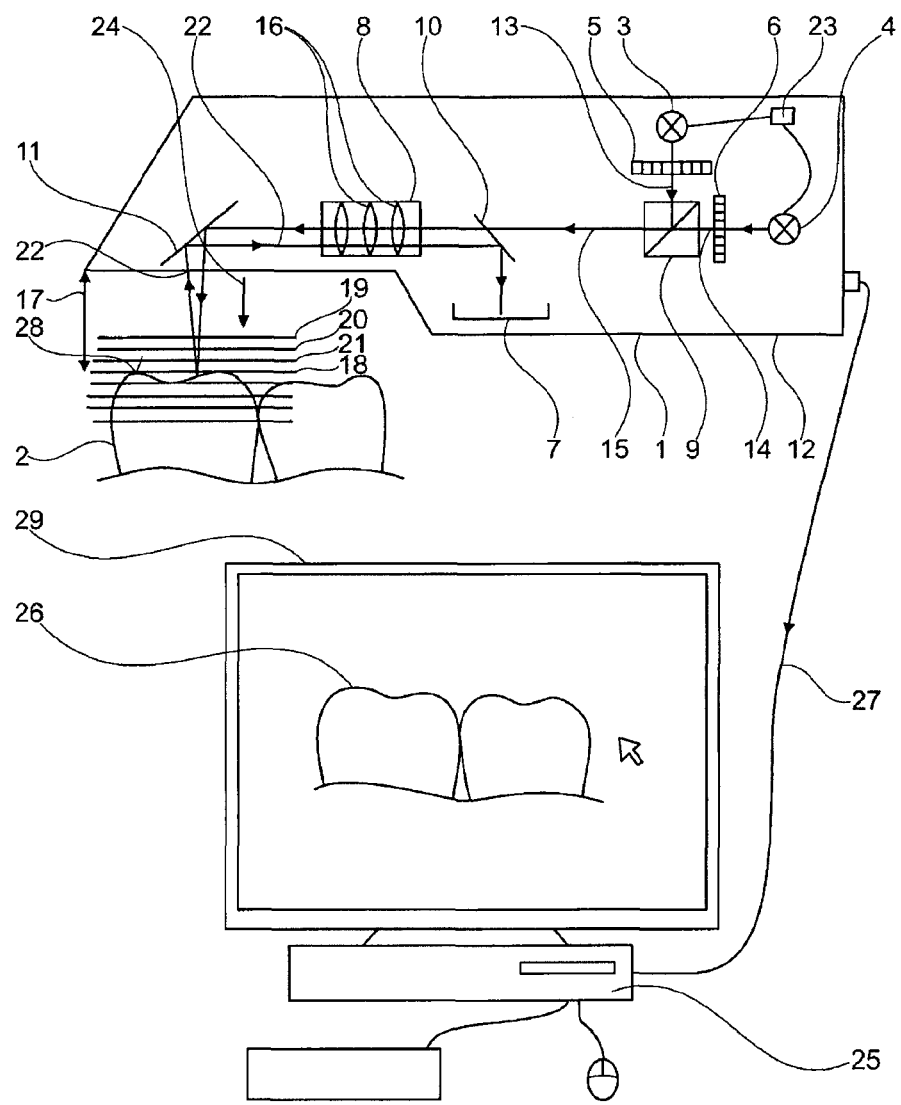
FIG. 1 shows a sketch of a device for optical 3D measurement of an object.

FIG. 1 shows a sketch of a device 1 for optical 3D measurement of an object 2. The device 1 is a handheld dental camera for measuring the objects 2, for instance a patient's teeth or a tooth model. The camera 1 comprises a first light source 3, a second light source 4, a first optical means 5, a second optical means 6 for producing textured patterns, a recording means 7, imaging optics 8, a first beam splitter 9, a second beam splitter 10, a mirror 11 and a housing 12. The light sources 3 and 4 can be realized as simple LEDs, colored LEDs, white LEDs or laser LEDs. The optical means 5 and 6 can be realized as optical gratings or as LCDs, which are controlled accordingly in order to produce the projected patterns. With the aid of the first optical means 5, the first pattern is projected and emitted in the direction of the first beam splitter 9 as a first projection beam 13. With the aid of the second optical means 6, the second pattern is emitted in the direction of the first beam splitter 9 as a second projection beam 14. By means of the first beam splitter 9, the projection beams 13 and 14 are deflected into one common illumination direction 15 toward the object 2. The recording means 7 is an optical sensor, such as a CCT sensor. The imaging optics 8 comprise a plurality of lenses 16, which are controlled in such a way that a focal distance 17 of a plane of sharp focus 18 relative to the camera 1 is incrementally adjusted between a plurality of defined scan positions 19, 20 and 21. For every scan position 18, 19, 20 and 21, a first image with the first projected pattern is produced and a second image with the second projected pattern is produced. The projected pattern can have a checkerboard-like shape, for example, or consist of a number of patterns. The projected pattern is thus projected onto the object 2 and is reflected back from the object 2 as an observation beam 22, deflected by means of the second beam splitter 10 and recorded with the aid of the recording means 7. The light sources 3 and 4 are activated in an alternating manner by means of a control 23, so that the first pattern and the second pattern are projected onto the object 2 in an alternating manner. The switching operation by means of the control 23 can be effected, for example, at a frequency of 8000 Hz. The scan positions 18, 19, 20 and 21 can be disposed, for example, at a distance of 0.1 mm from one another. The resolution along an optical axis 24 is thus defined by said distance between the scan positions. The checkerboard-like pattern can consist of a plurality of square light and dark pattern elements, wherein the width of one pattern element in the projection plane of the recording means 7 can correspond to the width of one pixel of the sensor being used. A first intensity value for a light pattern element and a second intensity value for a dark pattern element are thus determined for every pixel of the sensor, whereby a difference value between the first intensity value and the second intensity value can be determined by subtraction with the aid of an arithmetic unit 25, such as a computer. The arithmetic unit 25 can also be a microcomputer or a chip, that is integrated into the camera 1. The arithmetic unit 25 can also be an external computer. After each scanning procedure, the optical images produced for the different scan positions 18, 19, 20 and 21 are merged and a 3D data set 26 of the object 2 is generated from said images. The images can also be merged by means of another method using the arithmetic unit 25. A plurality of contrast values can be determined in the transition areas between the light and dark pattern elements, for example, and the depth information can be calculated from said values. The image data of the sensor 7 are read out after each optical recording, as indicated by the arrow 27, and transmitted to the arithmetic unit 25. After the complete measurement of the object 2, the determined coordinates of the measuring points on an object surface 28 are used to calculate the 3D data set 26. The 3D data set 26 is displayed by means of a display device 29, such as a monitor.

Figures 2, 3:
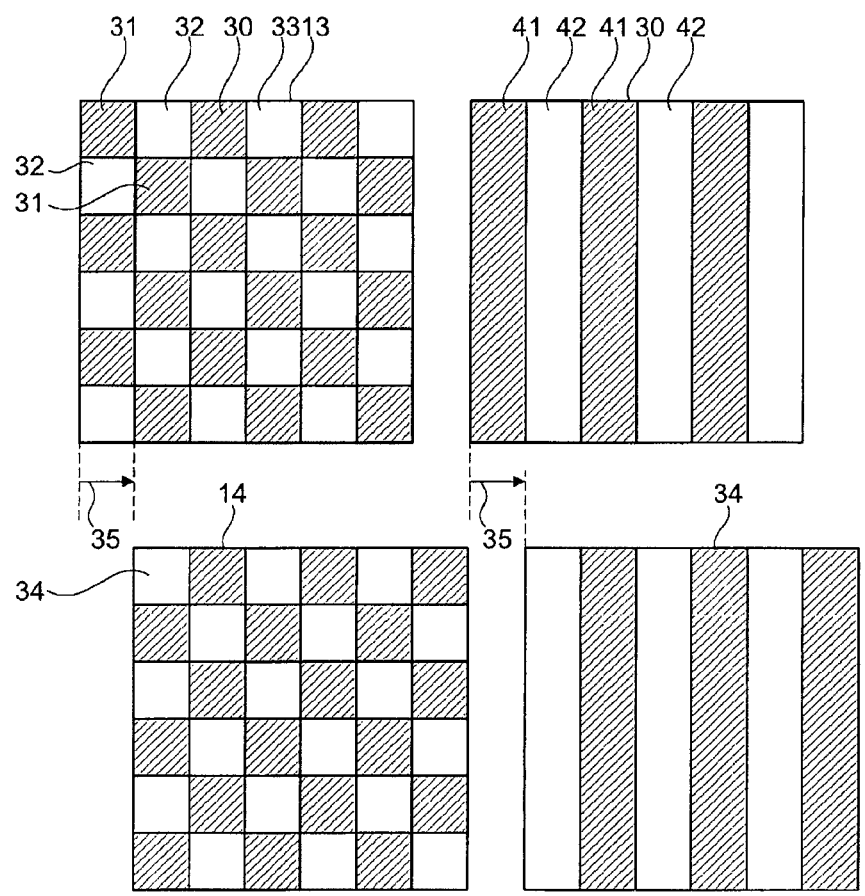
FIG. 2 shows a sketch of a checkerboard-like projection pattern.
FIG. 3 shows a sketch of a projection pattern which consists of dark stripes and light stripes.

FIG. 2 shows a sketch of a first checkerboard-like projected pattern 30, which is emitted by the first light source 3 as the first projection beam 13 and recorded by means of the sensor 7 in the first scan position 18 of FIG. 1. In their dimensions, the dark pattern elements 31 of the first projected pattern 30 and the light pattern elements 32 of the first projected pattern 30 correspond to the individual pixels 33 of the sensor 7. By switching off the first light source 3 and switching on the second light source 4, the second projected pattern 34, which is emitted by the second light source 3 as the second projection beam 14 and recorded by means of the sensor 7 in the first scan position 18 of FIG. 1, is thus projected onto the object 2. The first projected pattern 30 corresponds in shape to the second projected pattern 34, whereby the second pattern 34 is shifted laterally, whereby the displacement 35 corresponds to the width of a pixel 33. In this way, every pixel of the sensor 7 is illuminated in an alternating manner with a light pattern element 32 or a dark pattern element 31. From the first image of the first pattern 30 and from the second image of the second pattern 34, it is thus possible to determine an intensity value for one respective light and dark pattern element for every pixel. If the sharp layer coincides with the object surface 28 of the object 2, the projection pattern 30 is reproduced on the sensor 7 as a sharp image, so that the difference values of the intensity values for the individual pixels are at the maximum.

FIG. 3 shows a sketch of a first projection pattern 30, which consists of dark stripes 41 and light stripes 42. In comparison to the first projected pattern, as in FIG. 2, the second projected pattern 34 is shifted by a displacement 35, which corresponds to a pixel width of the sensor 7. As a result of activating the light sources 3 and 4 in an alternating manner, every pixel of the sensor 7 is illuminated in an alternating manner with a light stripe 42 or a dark stripe 41.

Figure 4:
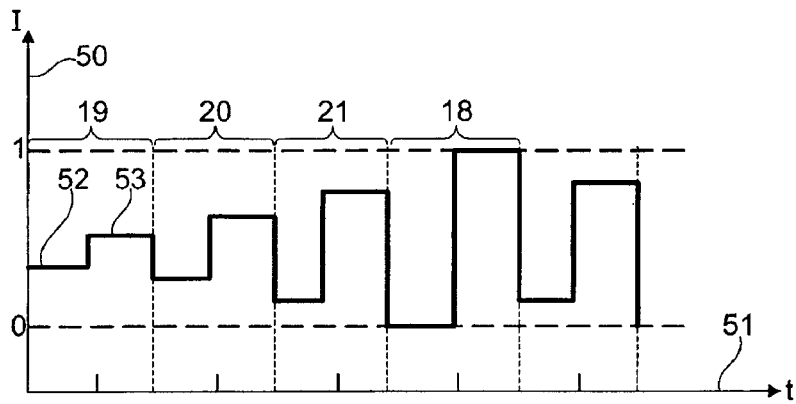
FIG. 4 shows a diagram of an intensity value as a function of time.

FIG. 4 shows a diagram of an intensity value 50 on the y-axis as a function of time 51 on the x-axis. During the illumination of the object with the first pattern 30, a first intensity value 52 on a scale between 0 and 1 is determined from the first image, and a second intensity value 53 is determined from the second image during the illumination of the object with the second pattern 34. The intensity values are determined for the scan positions 18, 19, 20 and 21 of FIG. 1.

Figure 5:
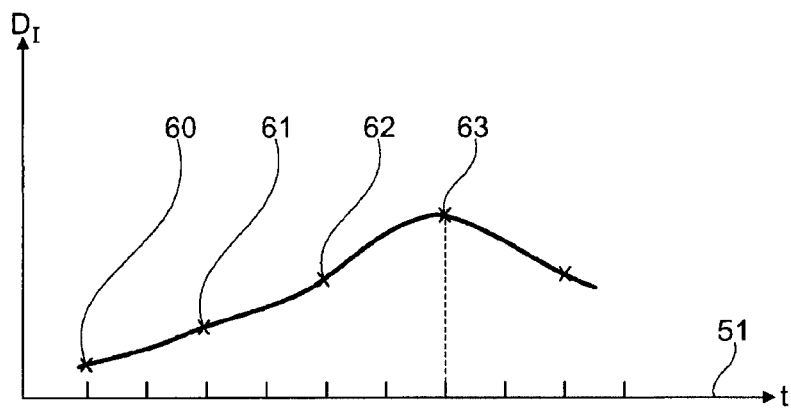
FIG. 5 shows a diagram of a difference value as a function of time.

FIG. 5 shows a diagram to illustrate the present method, wherein, by subtraction from the intensity value 52 and 53, a first difference value 60 is determined for the first scan position 19, a second difference value 61 is determined for the second scan position 20, a third difference value 62 is determined for the third scan position 21 and a fourth difference value 63 is determined for the fourth scan position 18. The difference values are plotted as a function of time 51. In the fourth scan position 18, the difference value 63 is at maximum, so that in this scan position 18 the plane of sharp focus 7 coincides with the surface 28 of the object. Depth information for the corresponding measuring point on the surface 28 of the object can thus be determined for every pixel.

Figure 6:
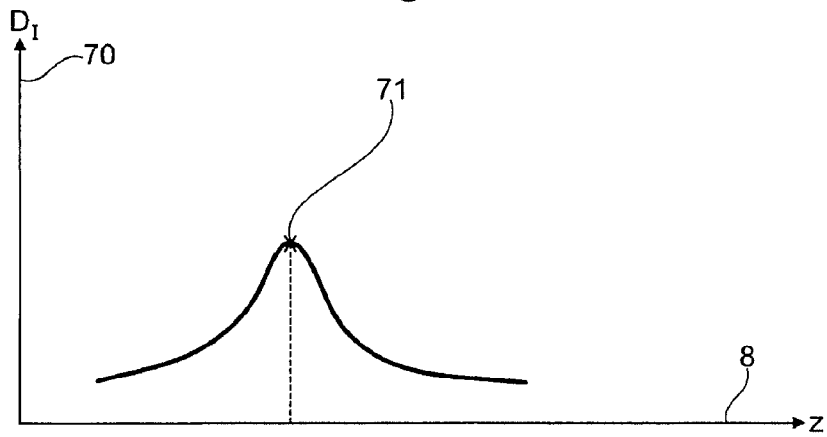
FIG. 6 shows a diagram of the difference value as a function of a focal distance.

FIG. 6 shows the difference value 70 as a function of the focal distance 17 for one individual pixel of the sensor 7. The contrast is at a maximum at a maximum 71 of the difference value, because the projection pattern 30, 34 of FIG. 2 is reproduced as a sharp image.

REFERENCE SIGNS 1 device
2 object
3 first light source
4 second light source
5 first optical means
6 second optical means
7 recording means
8 imaging optics
9 first beam splitter
10 second beam splitter
11 mirror
12 housing
13 first projection beam
14 second projection beam
15 illumination direction
16 lenses
17 focal distance
18 plane of sharp focus
18 scan position
19 scan position
20 scan position
21 scan position
22 observation beam
23 control
24 optical axis
25 arithmetic unit
26 3D data set
27 arrow
28 object surface
29 display device
30 first projected pattern
31 dark pattern elements
32 light pattern elements
33 pixel
34 second projected pattern
35 displacement
41 dark stripes
42 light stripes
50 intensity value
51 time
52 first intensity value
53 second intensity value
60 first difference value
61 second difference value
62 third difference value
63 fourth difference value
70 difference value

The invention claimed is:

1. A device for optical 3D measurement of an object using an optical depth-scanning measurement method, comprising:
   at least two light sources;
   at least two optical devices configured to produce textured patterns including a first optical device and a second optical device;
   at least one optical sensor;
   an imaging optics; and
   a first beam splitter,
   wherein the first optical device is configured to produce a first pattern and project said first pattern onto the object to be recorded as a first projection beam,
   wherein the second optical device is configured to produce a second pattern and project said second pattern onto the object to be recorded as a second projection beam, such that the first pattern and the second pattern are reflected back from the object as observation beams and recorded by the optical sensor in order to create a 3D data set of the object,
   wherein the imaging optics is configured to project the patterns onto the object, said imaging optics being controlled and adjusted such that a sharp focal plane is incrementally varied along an optical axis of the device, and such that at each scan position of the sharp focal plane, the first pattern is projected to produce a first optical image and the second pattern is projected onto the object to produce a second optical image,
   wherein the first light source and the second light source are configured to be activated in an alternating manner,
   the first beam splitter being configured to deflect the first projection beam of the first pattern and the second projection beam of the second pattern into one common illumination direction toward the object,
   wherein the optical depth-scanning measurement method is a depth-from-defocus measurement method (DFD),
   wherein light pattern elements and dark pattern elements of the two patterns are projected onto the object in an alternating manner, and
   wherein the device is configured to obtain 3D depth information of the object based on contrast values between the light and the dark elements of the patterns which are defined for each optical image.

2. The device according to claim 1, further comprising a third light source, a third optical device and a second beam splitter, wherein a third pattern is produced with the aid of the third optical device and a third projection beam is deflected into the common illumination direction with the aid of the second beam splitter.

3. The device according to claim 2, wherein the first beam splitter and the second beam splitter are combined into a dichroic prism,
wherein the first, second and third projection beam are deflected into the common illumination direction using the dichroic prism.

4. The device according to claim 1, wherein the at least two optical devices are optical gratings or liquid-crystal elements (LCD).

5. The device according to claim 1, further comprising a control that switches the light sources on and off in an alternating manner at a frequency of at least 3000 Hz.

6. The device according to claim 5, wherein the frequency advantageously lies between 5000 Hz and 10000 Hz.

7. The device according to claim 1, wherein at least 100 scan positions of a sharp focal plane are incrementally set and measured to produce the optical images or scans.

8. The device according to claim 7, wherein at least 200 scan positions of the sharp focal plane are set.

9. The device according to claim 1, wherein a profile of the contrast values is determined for each measuring point of the object for all the set scan positions of a plane of sharp focus, wherein a maximum value of this profile is subsequently determined, which represents the depth information of the object surface for this measuring point of the object.

10. The device according to claim 1, wherein the projected patterns exhibit the form of a checkerboard with square pattern elements or the form of parallel stripes.

* * * * *